United States Patent

Uehara et al.

Patent Number: 5,097,055
Date of Patent: Mar. 17, 1992

[54] PRODUCTION OF METHYLPHENYLTRISILOXANE

[75] Inventors: Katsuhiro Uehara; Toshinobu Ishihara, both of Joetsu; Jiyunitirow Maruta, Higashikubiki; Akira Hayashida, Higashimurayama, all of Japan

[73] Assignee: Shin-Etsu Chemical Co., Ltd., Tokyo, Japan

[21] Appl. No.: 680,696

[22] Filed: Apr. 4, 1991

[30] Foreign Application Priority Data

Apr. 5, 1990 [JP] Japan ................... 2-90685

[51] Int. Cl.⁵ .................................. C07F 7/08
[52] U.S. Cl. ................................... 556/453
[58] Field of Search ........................ 556/453

[56] References Cited

U.S. PATENT DOCUMENTS 3,133,110 5/1964 More-house et al. ............... 556/453

Primary Examiner—Paul F. Shaver
Attorney, Agent, or Firm—Nixon & Vanderhye

[57] ABSTRACT

A process of producing a methylphenyltrisiloxane having the following general formula:

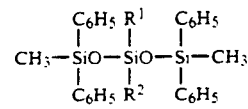

wherein $R^1$ and $R^2$ may be the same or different and are each a methyl or phenyl group, the process comprising the step of reacting:

(A) methyldiphenylsilanol, with
(B) a silazane compound having a diorganosilazane unit having the following formula:

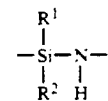

wherein $R^1$ and $R^2$ are as defined above. According to the process, colorless and odorless methylphenyltrisiloxanes can be obtained easily, safely and economically, without any special deodorizing or decoloring step.

8 Claims, No Drawings

PRODUCTION OF METHYLPHENYLTRISILOXANE

BACKGROUND OF THE INVENTION

1. Field of the Invention

This invention relates to a process of producing a methylphenyltrisiloxane having the following general formula [I]:

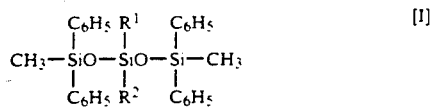

wherein $R_1$ and $R_2$ may be the same or different and are each a methyl or phenyl group.

2. Description of the Prior Art

Methylphenyltrisiloxanes having the above general formula [I], for example, 1,3,3,5-tetramethyl-1,1,5,5-tetraphenyltrisiloxane, are widely used as silicone oil for oil diffusion pumps and are of industrial use.

For the production of a methylphenyltrisiloxane having the general formula [I], there has been known, for example, a process in which methyldiphenylsilanol is condensed with dimethyldichlorosilane or methylphenyldichlorosilane with hydrochloric acid being eliminated in the presence of a dehydrochlorinating agent comprising an organic amine compound such as pyridine, trialkylamine, etc. to synthesize a methylphenyltrisiloxane compound having $R_1$ and $R_2$ corresponding to the diorganodichlorosilane used (Refer to U.S. Pat. No. 2,890,234 and Nakayama et al.: Shinkuh (Vacuum), 13(2), 59-63 (1970)).

Another process has also been known in which sodium methyldiphenylsilanolate is prepared from methyldiphenylsilane, and is reacted with dimethyldichlorosilane or diphenyldichlorosilane to produce a methylphenyltrisiloxane compound having $R^1$ and $R^2$ corresponding to the diorganodichlorosilane used (See U.S. Pat. No. 3,523,131).

However, the process according to U.S. Pat. No. 2,890,234 and the process by Nakayama et al. involve the use of an organic amine compound in excess of the amount stoichiometrically equivalent to the methyldiphenylsilanol to be reacted therewith, and requires a greater space in the reactor accordingly. In addition, these processes produce large amounts of solid amine hydrochlorides as by-products, with the resultant lowering in the stirrability of the reaction system. It has been necessary, therefore, to add a large amount of solvent to the reaction system in order to obviate the lowering in stirrability. With such requirements, the processes are very low in yield per unit volume of a reactor and extremely poor in productivity. Furthermore, the processes have the problem of complicated steps, because the large amounts of amine hydrochlorides must be treated and the synthesized methylphenyltrisiloxane, having an amine odor and a pale yellow or a yellow color, requires deodorizing and decoloring steps for conversion into an odorless and colorless product. Thus, these processes have difficulties as to economy and operability.

The method according to U.S. Pat. No. 3,523,131, on the other hand, has the problem that the synthesizing process is long and that gaseous hydrogen, which is flammable and very difficult to deal with, is generated in large amounts during the preparation of the sodium methyldiphenylsilanolate as an intermediate.

SUMMARY OF THE INVENTION

Accordingly, it is an object of this invention to provide a process of producing a methylphenyltrisiloxane more easily, safely and economically than the conventional processes.

According to this invention, there is provided a process of producing a methylphenyltrisiloxane having the aforementioned general formula [I]:

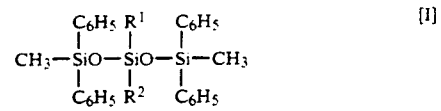

wherein $R^1$ and $R^2$ may be the same or different and are each a methyl or phenyl group, which comprises reacting:

(A) methyldiphenylsilanol, with (B) a silazane compound having a diorganosilazane unit having the following formula [II]:

wherein $R^1$ and $R^2$ are as defined above.

The process according to this invention is high in yield per unit volume of a reactor because of the freedom from the formation of solid by-products, which has been one of the major problems in the conventional processes. Further, most of the raw materials used in the process of this invention are easily available at low cost and in large quantities, rendering the process very advantageous on an economic basis.

Besides, the reaction by-product in the process of this invention is only gaseous ammonia, which is stripped out of the reaction system while the reaction mixture is matured under reflux and can be disposed of easily, for example, by neutralization after trapping with a water trap. Therefore, the process according to this invention is extremely safe to carry out, as compared with the conventional processes involving the generation of the flammable hydrogen gas, and requires no special after-treatment step.

According to this invention, furthermore, it is possible to obtain a colorless, odorless methylphenyltrisiloxane without any special decoloring or deodorizing step.

DETAILED DESCRIPTION OF PREFERRED EMBODIMENTS

Starting materials

In the process according to this invention, (A) methyldiphenylsilanol and (B) a silazane compound comprising a diorganosilazane unit having the aforementioned formula [II]are used as starting materials.

(A) Methyldiphenylsilanol

Methyldiphenylsilanol, one of the starting materials, is a known compound, for which there are known a variety of industrial production processes and which is easily available in large amounts and at low cost. In this point, the process of this invention has a great advantage over the conventional processes in which very expensive methyldiphenylsilane is used as a starting material.

(B) Silazane compound

The silazane compound, the other one of the starting materials, may be any silazane compound comprising a structural unit of the aforementioned formula [II], namely:

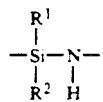
[II]

wherein $R_1$ and $R_2$ are as defined above. The silazane compound may be a cyclic compound, a linear compound or a mixture thereof.

The silazane compound includes, for example, a cyclic one having the following general formula [IIa]:

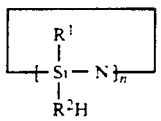
[IIa]

wherein $R^1$ and $R^2$ are as defined above, and n is an integer of 3 or 4, and a linear one comprising a block having the following general formula [IIb]:

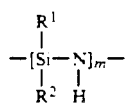
[IIb]

wherein $R^1$ and $R^2$ are as defined above, and m is an integer of from 1 to 10,000.

Such a silazane compound can be produced by known methods, for example, by reacting a diorganodichlorosilane having the following formula [III]:

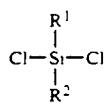
[III]

wherein $R^1$ and $R^2$ are as defined above, with ammonia. The resultant reaction product consists mainly of cyclic trimers and cyclic tetramers having the aforementioned general formula [IIa] and further comprises high polymeric linear silazane mixture compounds having a block of the aforementioned general formula [IIb]. The cyclic trimers and tetramers can be separately isolated from the silazane mixture by such means as distillation, whereas the high polymeric linear compounds are stable only in the equilibrium mixture upon the reaction and are generally difficult to isolate. In the process of this invention, however, the silazane compound composed of the structural units of the aforementioned formula [II] need not consist of a single compound, insofar as the structural units are identical. Therefore, it is unnecessary to isolate each of the cyclic compounds and linear compounds from the mixture of the reaction products of diorganodichlorosilane with ammonia, and the reaction product mixture can be used as it is. This is a major merit of the process according to this invention.

Synthesis reaction

In the process of this invention, the desired methylphenyltrisiloxane is synthesized by reacting the aforementioned methyldiphenylsilanol (A) with the silazane compound (B).

This synthesis reaction is represented by the following formula:

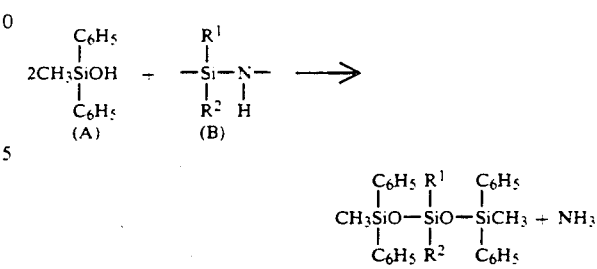

In the synthesis reaction, it is generally desirable to use the reactant silazane compound (B) in such an amount that the diorganosilazane unit of the formula [II] in the silazane compound (B) is present in an amount of not more than 0.5 mole, particularly from 0.45 to 0.5 mole, per mole of the methyldiphenylsilanol (A). If the amount of the silazane compound used is above the range, high-boiling intermediates with unreacted silazane linkage portions will be left in the reaction products, which is undesirable from the viewpoint of quality of the methylphenyltrisiloxane obtained and from an economic point of view. Use of an excessively small amount of the silazane compound, on the other hand, increases the amount of the methyldiphenylsilanol left unreacted, which is also undesirable economically.

It is generally preferable that the synthesis reaction is carried out by use of a suitable catalyst for completing the reaction in a short time, and under reflux of an organic solvent.

The above synthesis reaction can be conducted in various manners. Although methods therefor are not limited, the following two methods are particularly preferred.

Method 1:

All of methyldiphenylsilanol (A), the silazane compound (B), the catalyst and an organic solvent are placed together in a reactor, the mixture is heated to the reflux temperature of the solvent with stirring and then matured at the temperature.

Method 2:

The silazane compound (B), the catalyst and an organic solvent are placed in a reactor, the mixture is then heated to the reflux temperature with stirring. Methyldiphenylsilanol (A) is then gradually added dropwise to the reaction mixture with the temperature being maintained. After the addition, the reaction mixture is matured under the same conditions.

While Method 1 is simpler, in addition to the desired methylphenyltrisiloxane, methylphenylsiloxane compounds may be by-produced. In that case, Method 2 is more advantageous in that it can enhance selectivity in reaction to lower the amounts of the by-products.

The suitable catalysts include, for example, ammonium salts, and those acids or salts thereof other than ammonium salts thereof which are capable of forming an ammonium salt with ammonia generated in the reaction system.

The ammonium salts for use as the catalyst include, for example, ammonium fluoride, ammonium chloride, ammonium bromide, ammonium iodide, ammonium acetate, ammonium hydrogen carbonate, ammonium hydrogen sulfate, ammonium sulfate, ammonium carbonate, and ammonium arylsulfonates having the following general formula [IV]:

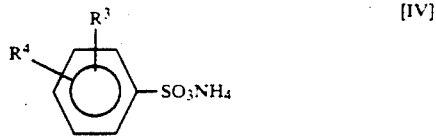

wherein $R^3$ and $R^4$ may be the same or different and are each hydrogen, a hydrocarbon group or an amino group, or $R^3$ and $R^4$ may be combined with each other into a divalent unsaturated hydrocarbon group to form a substituted or unsubstituted aromatic ring together with a part of the benzene ring in the formula [IV]. Specific examples of the ammonium arylsulfonates include ammonium benzenesulfonate, ammonium p-toluenesulfonate, ammonium m- or p-xylenesulfonate, ammonium o-, m- or p-aminobenzenesulfonate, ammonium dodecylbenzenesulfonate, ammonium aminonaphthalenesulfonate, etc.

The acids or salts thereof capable of forming an ammonium salt include, for example, acids or salts thereof corresponding to the aforementioned ammonium salts, such as hydrochloric acid, sulfuric acid, acetic acid, carbonic acid, etc.; acids or salts thereof corresponding to the ammonium arylsulfonates of the above general formula [IV], such as benzenesulfonic acid, p-toluenesulfonic acid, m-or p-xylenesulfonic acid, o-, m- or p-aminobenzenesulfonic acid, o-toluidine-p-sulfonic acid, m-toluidine-p-sulfonic acid, p-toluidine-m-sulfonic acid, dodecylbenzenesulfonic acid, aminonaphthalenesulfonic acid, and so on.

Of the aforementioned catalysts for use in this invention, the arylsulfonates are particularly preferred in view of their high catalytic activity and availability. Besides, the ammonium salt either added to the reaction system or formed by the reaction can be removed easily by water washing or filtration, and therefore does not affect the subsequent steps.

The catalyst is generally used in an amount of preferably from 0.1 to 10% by weight, more preferably from 0.5 to 5% by weight, based on the methyldiphenylsilanol (A). If the amount of the catalyst is less than 0.1% by weight, the rate of the synthesis reaction is low. On the other hand, use of the catalyst in an amount of more than 10% by weight do not produce a correspondingly increased effect and is disadvantageous on an economic basis.

According to this invention, the aforementioned reaction is preferably carried out under reflux of an organic solvent, whereby the by-produced ammonia can be stripped efficiently out of the reaction system, leading to smooth shift of the equilibrium of reaction toward the reaction products and to completion of the reaction in a short time. Therefore, the amount of the organic solvent to be used is not limited particularly, and may be set in such a range as to permit reflux in the reaction system. In general, the amount of the organic solvent is preferably about 50 to 100 ml per mole of methyldiphenylsilanol. Use of an excess of organic solvent will not only be disadvantageous economically but result in a lowered yield per unit volume of a reactor.

As the organic solvent for use in the synthesis reaction, liquid hydrocarbons being inactive to the reactants and having a boiling point of from 40° to 200° C. can be used, without any particular limitation. Among others, aromatic hydrocarbon solvents are especially preferable because their lack of active protons render them inactive to silazanes, their comparatively high boiling point enables a high reaction temperature to be employed, and they show high solubilities of the reactants and reaction products therein. Examples of such organic solvents include benzene, toluene, o-xylene, m-xylene, mixed xylene, ethylbenzene, mesitylene, petroleum ether, ligroin, kerosine, etc.

The synthesis reaction in this invention is ordinarily carried out under reflux of the organic solvent, so that the reaction temperature depends on the boiling point and the amount of the solvent used. It is generally desirable to set the reaction temperature in the range from 40° to 200° C., particularly from 110° to 160° C. Carrying out the reaction in such a temperature range offers the industrially favorable effects of shortening the operation time and permitting the use of a general-purpose heating medium.

Furthermore, it is preferable in this invention to carry out the synthesis reaction substantially in the absence of water and in a helium, nitrogen, argon or other inert gas atmosphere, in order to prevent side-reactions such as hydrolysis.

Reaction product

After the reaction is over, the reaction system is washed with water or filtrated to remove the organic solvent from the organic layer. Then the residue is subjected to a purification process such as distillation, whereby methylphenyltrisiloxane of the above general formula [I] is obtained in a colorless and odorless form.

The methylphenyltrisiloxane thus obtained may be 1,3,3,5-tetramethyl-1,1,5,5-tetraphenyltrisiloxane, 1,3,5-trimethyl-1,1,3,5,5-pentaphenyltrisiloxane, 1,5-dimethyl-1,1,3,3,5,5-hexaphenyltrisiloxane, or the like, depending on the kind of the organo group in the diorganosilazane unit possessed by the silazane compound (B) used as a starting material.

EXAMPLES

Example 1

A 1-liter 4-necked flask equipped with a stirrer, a thermometer and a water-cooled condenser was supplied with a sufficient flow therethrough of nitrogen, and then charged with 278.7 g (1.3 mol) of methyldiphenylsilanol, 47.6 g (0.217 mol) of hexamethylcyclotrisilazane, 5.57 g of ammonium sulfate and 100 ml of toluene. The resultant mixture was heated to a temperature of from 140° to 145° C. with stirring in a nitrogen atmosphere. With the temperature maintained, maturing was carried out under reflux for 10 hours. At this point, the composition of the reaction mixture was analyzed by gas chromatography, which showed that the methyldiphenylsilanol had been reacted completely.

Next, the reaction mixture was washed twice with 260 ml of water, and an organic layer was separated off. Then toluene was stripped, and the residue was subjected to distillation, whereby 296.4 g of the desired product 1,3,3,5-tetramethyl-1,1,5,5-tetraphenyltrisiloxane was obtained (yield 94.2%). The product thus obtained was odorless, colorless and transparent.

Example 2

A synthesis reaction was carried out in the same manner as in Example 1 except that ammonium chloride was used in place of ammonium sulfate. The reaction was completed after 10 hours of reaction under reflux, to give 288.0 g of 1,3,3,5-tetramethyl-1,1,5,5-tetraphenyltrisiloxane (yield 91.5%).

Example 3

A synthesis reaction was carried out in the same manner as in Example 1 except that p-toluenesulfonic acid was used in place of ammonium sulfate. The reaction was completed after 10 hours of reaction under reflux, to give 291.2 g of 1,3,3,5-tetramethyl-1,1,5,5tetraphenyltrisiloxane (yield 92.4%).

Example 4

A synthesis reaction was carried out in the same manner as in Example 1 except that p-toluenesulfonic acid was used in place of ammonium sulfate. The reaction was completed after 10 hours of reaction under reflux, to give 284.6 g of 1,3,3,5-tetramethyl-1,1,5,5-tetraphenyltrisiloxane (yield 90.4%). Example 5

A synthesis reaction was carried out in the same manner as in Example 1 except that 1.39 g of p-toluidinemsulfonic acid was used in place of 5.57 g of ammonium sulfate. The reaction was completed after 2 hours of reaction under reflux. After the catalyst was filtered off from the reaction mixture, toluene was stripped out, and the residue was subjected to distillation, whereby 301.3 g of 1,3,3,5-tetramethyl-1,1,5,5-tetraphenyltrisiloxane was obtained (yield 95.7%).

Example 6

A synthesis reaction was carried out in the same manner as in Example 1 except that o-xylene was used in place of toluene. The reaction was completed after 10 hours of reaction under reflux, to give 294.3 g of 1,3,3,5-tetramethyl-1,1,5,5-tetraphenyltrisiloxane (yield 93.5%).

Example 7

A synthesis reaction was carried out in the same manner as in Example 1 except that octamethylcyclotetrasilazane was used in place of hexamethylcyclotrisilazane. The reaction was completed after 10 hours of reaction under reflux, to give 278.0 g of 1,3,3,5-tetramethyl-1,1,5,5-tetraphenyltrisiloxane (yield 88.3%).

Example 8

(1) A 1-liter 4-necked flask equipped with a stirrer, a thermomemter and a water-cooled condenser was supplied with a sufficient flow therethrough of nitrogen, and then charged with 83.9 g (0.65 mol) of dimethyldichlorosilane and 325 ml of toluene. While the resultant mixture was stirred, an $NH_3$ gas was fed into the mixture at 20° to 30° C., upon which white crystals of ammonium chloride gradually separated out from the reaction mixture. The reaction was continued with sampling at appropriate times, and was finished when it was confirmed that dimethyldichlorosilane was completely lost. To the reaction mixture was added 280.8 g of 20% aqueous NaOH solution at room temperature, so that ammonium chloride was completely dissolved. Then, the upper organic layer was separated, and toluene was stripped out.

The reaction product thus obtained was a dimethylsilazane mixture consisting mainly of hexamethylcyclotrisilazane and octamethylcyclotetrasilazane.

(2) Next, a 1-liter 4-necked flask equipped in the same fashion as above was supplied with a sufficient flow therethrough of nitrogen, and then charged with the aforementioned dimethylsilazane mixture (containing dimethylsilazane units in an amount equivalent to 0.65 mol), 278.7 g (1.3 mol) of methyldiphenylsilanol, 5.57 g of ammonium sulfate and 100 mol of toluene. The resultant mixture was heated to a temperature of from 140° to 145° C., and maturing was carried out under reflux for 10 hours. After the maturing was over, the composition of the reaction system was analyzed by gas chromatography, which showed that the methyldiphenylsilanol had been completely reacted.

After the reaction mixture was then washed with water and concentrated, the residue was subjected to distillation, to give 292.1 g of the desired product 1,3,3,5-tetramethyl-1,1,5,5-tetraphenyltrisiloxane (yield 92.8%).

Example 9

A synthesis reaction was carried out in the same manner as in Example 8 except that 1.39 g of p-toluidienmsulfonic acid was used in place of 5.57 g of the ammonium sulfate and that the reaction mixture after maturing was not washed with water as in Example 8 (2) but filtered. The reaction was completed after 2 hours of reaction under reflux, to give 259.5 of 1,3,3,5-tetramethyl-1,1,5,5-tetraphenyltrisiloxane (yield 94.0%).

Example 10

(1) Synthesis of a silazane compound was carried out in the same manner as in Example 8 (1) except that 124.2 g (0.65 mol) of methylphenyldichlorosilane was used in place of 83.9 g (0.65 mol) of dimethyldichlorosilane, to yield a silaxane mixture consisting mainly of 1,3,5-trimethyl1,3,5-triphenylcyclotrisilazane and 1,3,5,7-tetramethyl-1,3,5,7-tetraphenylcyclotetrasilazane.

(2) Next, a 1-liter 4-necked flask equipped in the same fashion as above was supplied with a sufficient flow therethrough of nitrogen, and then charged with the aforementioned methylsilazane mixture (containing methylphenylsilazane units in an amount of to 0.65 mol), 1.39 g of dodecylbenzenesulfonic acid and 100 ml of toluene. The resultant mixture was heated to a temperature of from 140° to 145° C., and continuously heated under reflux. subsequently, 278.7 g (1.3 mol) of methyldiphenylsilanol was added dropwise thereto over 4 hours, followed by maturing under reflux for 3 hours to complete the reaction. After the reaction mixture was then washed with water and concentrated, the residue was subjected to distillation, to give 320.4 g. of the desired product 1,3,5-trimethyl-1,1,3,5,5-pentaphenyltrisiloxane (yield 90.2%).

EXAMPLE 11

Synthesis of methylphenyltrisiloxane was carried out in the same manner as in Example 10 except that 1.39 g of p-toluidine-m-sulfonic acid was used in place of 1.39 g of dodecylbenzesulfonic acid, to give 324.3 g of 1,3,5-trimethyl-1,1,3,5,5-pentaphenyltrisiloxane (yield 91.3%).

EXAMPLE 12

Synthesis of a silazane compound was carried out in the same manner as in Example 8 (1) except that diphenyldichlorosilane was used in place of dimethyldichlorosilane, to yield a silazane mixture consisting mainly of hexaphenylcyclotrisilazane and octaphenylcyclotetrasilazane.

Synthesis of methylphenyltrisiloxane was carried out in the same manner as in Example 10 (2) except that the silazane mixture obtained as above was used, to give 354.0 g of 1,5-dimethyl-1,1,3,3,5,5-hexaphenyltrisiloxane (yield 89.5%).

We claim:

1. A process of producing a methylphenyltrisiloxane having the following general formula:

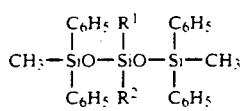  [I]

wherein $R^1$ and $R^2$ may be the same or different and are each a methyl or phenyl group, which comprises reacting:

(A) methyldiphenylsilanol, with (B) a silazane compound having a diorganosilazane unit having the following formula:

wherein $R^1$ and $R^2$ are as defined above.

2. The process according to claim 1, wherein the silazane compound (B) is a cyclic compound having the general formula:

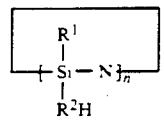  [IIa]

wherein $R^1$ and $R^2$ are as defined above, and n is integer of 3 or 4.

3. The process according to claim 1, wherein the silazane compound (B) is a linear compound comprising a block having the general formula:

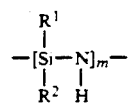  [IIb]

wherein $R^1$ and $R^2$ are as defined above, and m is an integer of from 1 to 10,000.

4. The process according to claim 1, wherein the silazane compound (B) is a reaction product of a diorganodichlorosilane having the general formula:

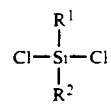  [III]

wherein $R^1$ and $R^2$ are as defined above, with ammonia.

5. The process according to claim 1, wherein the silazane compound (B) is used in such an amount as to supply not more than 0.5 mole of the diorganosilazane unit of the formula per mole of the methyldiphenylsilanol (A).

6. The process according to claim 1, wherein the methyldiphenylsilanol (A) is reacted with the silazane compound (B) in the presence of a catalyst, the catalyst comprising an ammonium salt or comprising an acid or salt thereof other than ammonium slat thereof which is capable of forming an ammonium salt.

7. The process according to claim 6, wherein the catalyst is used in an amount of from 0.1 to 10% by weight based on the methyldiphenylsilanol (A).

8. The process according to claim 1, wherein the reaction is carried out in an organic solvent at a temperature of from 40° to 200° C.

* * * * *